United States Patent [19]

Lloyd et al.

[11] Patent Number: 4,725,964

[45] Date of Patent: Feb. 16, 1988

[54] COMPUTER CONTROLLED ADAPTER UNIT FOR FLUID SYSTEM CONTROL

[75] Inventors: Geoffrey R. Lloyd, Richmond; Roy L. Tranter, Barnard Castle; Peter B. Stockwell, Westerham, all of England

[73] Assignee: Glaxo Group Limited, London, England

[21] Appl. No.: 696,330

[22] Filed: Jan. 30, 1985

[30] Foreign Application Priority Data

Jan. 31, 1984 [GB] United Kingdom ............... 8402538

[51] Int. Cl.⁴ .............................................. G01F 1/00
[52] U.S. Cl. .................................. 364/509; 364/510; 73/861.08
[58] Field of Search ................. 364/496–500, 364/509–511, 413–416, 138, 188, 189, 478, 479; 435/1, 289, 291; 604/50, 66; 222/52, 56; 73/861.08

[56] References Cited

U.S. PATENT DOCUMENTS

| | | | |
|---|---|---|---|
| 3,560,161 | 3/1968 | Clark et al. | 422/81 |
| 4,176,395 | 11/1979 | Evelyn-Veere et al. | 364/510 |
| 4,204,037 | 5/1980 | Dill et al. | 435/291 |
| 4,280,494 | 7/1981 | Cosgrove, Jr. et al. | 604/50 |
| 4,308,866 | 1/1982 | Jelliffe et al. | 364/413 |
| 4,333,356 | 6/1982 | Bartels et al. | 73/864.21 |
| 4,339,699 | 7/1982 | de Jonge et al. | 318/561 |
| 4,392,849 | 7/1983 | Petre et al. | 364/510 |
| 4,562,552 | 12/1985 | Miyaoka et al. | 364/510 |
| 4,573,114 | 2/1986 | Ferguson et al. | 364/510 |
| 4,581,707 | 4/1986 | Millar | 364/510 |

FOREIGN PATENT DOCUMENTS

| | | |
|---|---|---|
| 0083474 | 2/1981 | European Pat. Off. . |
| 2818302 | 11/1978 | Fed. Rep. of Germany . |
| 1579212 | 7/1969 | France . |
| 1249126 | 10/1971 | Luxembourg . |
| 1595885 | 8/1981 | United Kingdom . |

OTHER PUBLICATIONS

PCT Application: Gruenberg, Michael L., "Apparatus for Delivering a Controlled Dosage of a Chemical Substance", Jan. 5, 1984, PCT/US83/00865.

Primary Examiner—Parshotam S. Lall
Assistant Examiner—Brian M. Mattson
Attorney, Agent, or Firm—McAulay, Fields, Fisher, Goldstein & Nissen

[57] ABSTRACT

A unit is disclosed which enables computer operation of and data acquisition from a system requiring a fluid input and supplying data in electrical form at an output. The unit comprises a valve for supply of fluid between one and a plurality of selectable ports. A valve actuator brings the one port and a selected port into communication in response to a signal derived from a micro-computer. An A/D converter relays data derived from said system to the micro-computer in digital form.

The unit is preferably adapted for communication with an external computer to permit programming of the micro-computer and data acquisition by this computer.

13 Claims, 8 Drawing Figures

COMPUTER CONTROLLED ADAPTER UNIT FOR FLUID SYSTEM CONTROL

BACKGROUND OF THE INVENTION

The present invention relates to a unit permitting computer operation of and data acquisition from liquid testing/handling apparatus.

In the pharmaceutical industry, for example, measurement accuracy is of great importance both in the research laboratory and the production line. This has led naturally to the development of complex and expensive dedicated test systems in which accuracy has taken precedence over automation.

An example of this can be seen in those commercial systems developed for dissolution rate analysis, and which are employed as an important adjunct to tablet assays. Such systems are rigidly defined, their operation being restricted to a set number of dissolution baths and specific types of end point measurement. For example, in those systems employing a spectrophotometer, solution from each of six baths is supplied to a respective quartz cell for analysis. Each cell is moved past a detector and the readings obtained for each cell are supplied in analogue voltage form to a dedicated display and/or recording device. Thus, in addition to being technically complex and expensive, such systems are limited to semi-automatic batch operation. Further, they are not readily adapted to continuous or automatic processing and have no provisions to permit automatic control of the take-up or passage of liquid through the cells in relation to the data contained in the output signal derived from the detector.

SUMMARY OF THE INVENTION

An object of the present invention is to provide means enabling integration of commercially available dedicated apparatus of systems employing a fluid input and supplying test operational/data in an electrical form at an output, into respective computer controlled systems.

According to the present invention there is provided a unit enabling computer operation of and data acquisition from a system requiring a fluid input and supplying data in electrical form at an output, said unit comprising valve means for supply of fluid between one and a plurality of selectable ports; valve actuating means for bringing said one port and a selected port into communication in response to a signal derived from the computer and means for relaying data derived from said system to said computer in digital form.

The data transfer to the computer may be, for example, the results of a test and/or for the purpose of operational and/or corrective/emergency control of the system.

In a preferred embodiment, the unit comprises microcomputer means for local program storage and control of the valve. Depending on the capacity, programming and desired application, these micro-computer means and hence, the unit may operate in conjunction with an external computer or entirely alone. In the latter case, the unit provides a self-contained computerized controller.

Means are preferably provided for programming the micro-computer and may comprise an input for connection with an external computer data bus and/or a keyboard integral with the unit.

The output signal of test/monitoring apparatus is preferably used in the control of the valve. Thus, in one embodiment of the present unit, the data of this output signal is itself monitored so that the valve is only switched to a selected subsequent port setting once a stable reading is attained by this apparatus.

The ability to monitor the output of test/monitoring apparatus not only allows for feed-back control of the systems operation but also the production of warning signals when pre-determined tolerances are exceeded and, in addition, for continuous recording of its operation for subsequent analysis and/or use in quality control.

Where the output of the test/monitoring apparatus is in analog voltage form, the signal is fed to the computer (i.e. internal and/or external computer, as appropriate) via an analogue to digital converter forming a part of the unit.

Means are preferably provided for monitoring the actual status of the valve so that should this not correspond with that desired, corrective measures can be taken to drive the valve to the desired position. Further, the information regarding the status of the valve throughout operation is preferably also relayed to an external computer for storage and reference during analysis of the test/operational data.

A pump is preferably provided integral with the unit and its operation controlled by the computer.

Means are preferably provided to allow for manual operation of the valve in addition to the control exercised by the computer.

The valve ports are preferably provided with input-/output connector tubes which have filters to prevent blockage of the valve by extraneous material.

Embodiments of the present invention will now be described, by way of example, with reference to the accompanying drawings.

DESCRIPTION OF PREFERRED EMBODIMENTS

Figure 1:
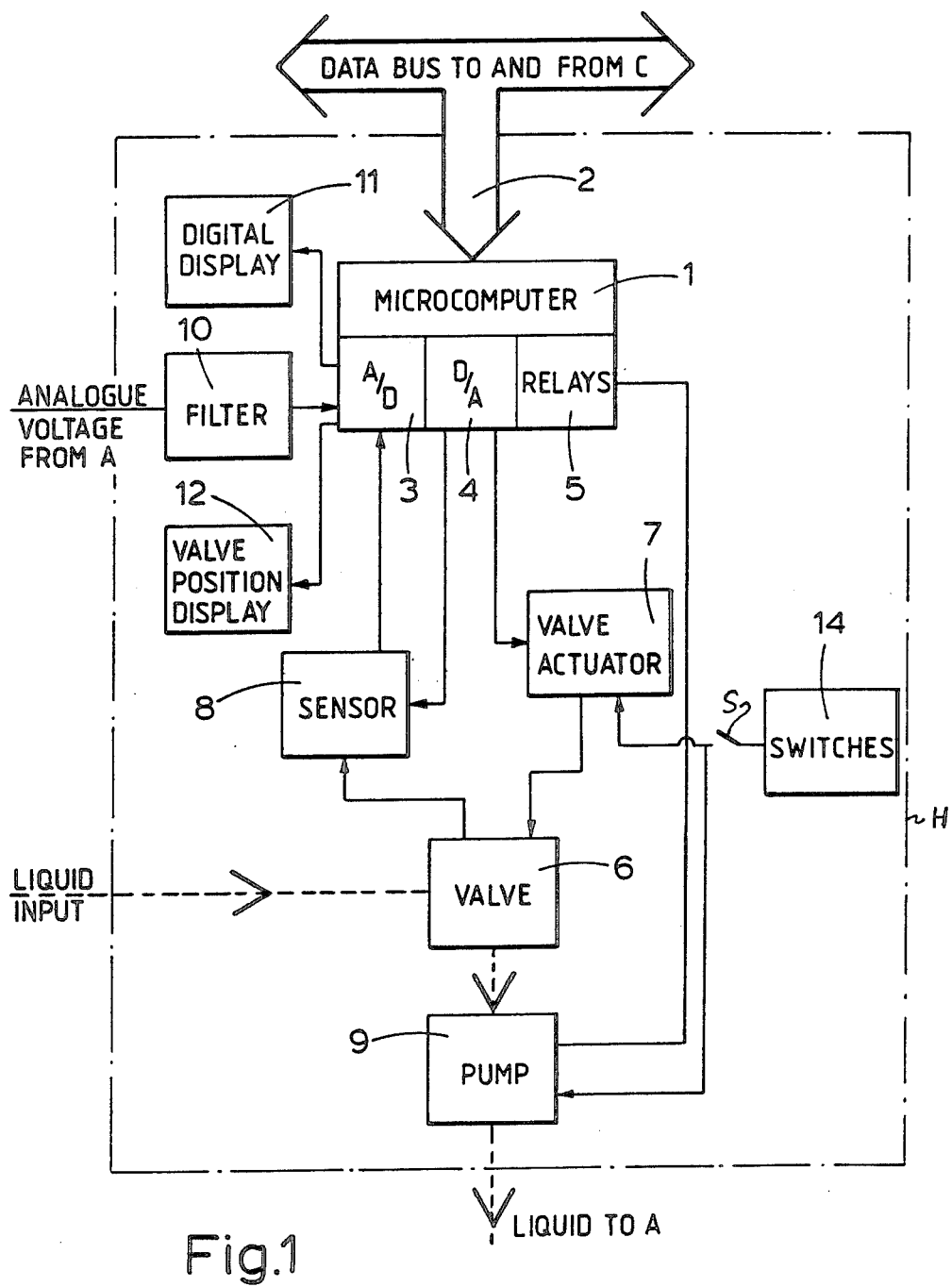
FIG. 1 shows a block diagram illustrating one embodiment of the invention.

The unit U shown in FIG. 1 comprises a micro-computer 1 and associated bus 2 for transferring signals to and from an external computer C which, along with the other elements comprising the unit, are housed within a housing indicated diagrammatically by the dashed line H. This micro-computer 1 directly controls the operation of and acquisition of data from a test/monitoring apparatus A by means of support devices. These support devices include an analog to digital converter 3, a digital to analog converter 4 and relays 5.

A valve 6 which has a low dead volume, is provided for the supply of fluid to the test apparatus A. The setting of this valve 6 is controlled by means of signals provided in an output of the digital to analog converter 4 and derived from the micro-computer 1. These signals operate a pneumatic valve actuator 7 which drives the valve 6 between selected port settings in desired sequence.

The valve 6 of this embodiment has ten randomly selectable ports and is composed of a material inert to aqueous solutions, 0.1 M hydrochloric acid, aliphatic alcohol and acetone, for example, Teflon ("Teflon" is a Trademark). Each port is provided externally with connector tubes having filters to prevent the entrance of extraneous material to the valve 6.

A potentiometer associated with the valve 6 is used as a sensor 8 to determine the actual status of the valve 6 on request from the micro-computer 1 via the D/A converter 4. The output of this sensor 8 is supplied to the micro-computer 1 via an input to the analog to digital converter 3, which compares the actual status of the valve with that determined by its program. Should there be a discrepancy, further signals are sent by the micro-computer 1 to the valve actuator 7 via the D/A converter 4 until the desired setting is achieved.

A reversible pump 9 draws liquid through the valve in a predetermined direction in response to commands derived from the micro-computer 1 and supplied via the relays 5. The provision of a reversible pump not only permits liquid to be supplied to the test apparatus from a selected one of the plurality of ports via the single port or vice versa as required, but also the return of liquid to its original container after testing in the test apparatus A. Further, this flow reversal through the valve may be used to remove extraneous material lodging on any of the port filters.

By control of the pump 9 via the relays 5, liquid may be supplied to the test apparatus A in a continuous stream or in measured quantities.

In addition to being operable by means of the micro-computer 1, the pump 9 and valve actuator 7 are both manually operable by means of switches 14 provided on the unit housing. This enables initial testing of the valve and pumping system from this local keyboard prior to automatic operation. During automatic operation the keyboard is disabled by a switch S but it may be reactivated should emergency intervention be required.

The data contained in analog voltage signals at an output of the test apparatus A is supplied to the micro-computer 1 via an input to the analog to digital converter 3. An electronic filter 10 is provided at this input to remove extraneous signals from that supplied.

In this embodiment, this input channel has a resolution which is compatible with a large number of test apparatus without the need for gain adjustments. However, amplifying means (not shown) are provided to enable gain adjustments should this be necessary.

The micro-computer 1 supplies data derived from its various inputs to digital displays for display in a predetermined format. In the present embodiment, a digital display 11 displays the magnitude of the incoming analogue voltage signals and a display 12, the valve port position.

Specifications for the pump, micro-computer and support devices of this embodiment are given below, by way of example:

Pump: Peristaltic—capable of pumping aqueous solution at up to 15 mililitres per minute to 0.016" (0.41 mm) internal diameter tube.

Valve Port Connection: 1/16" (1.59 mm) into ¼" (6.36 mm)×28 standard flanged fitting connector.

Micro-computer: Z80 micro-computer controlled from 4K EPROM and having 6K of RAM for data collection and program use. (A further 32 RAM can be provided for extra data and programme storage)

Bus: IEEE 488 bus capable of supporting serial poll interrupt sequences

A/D Converter: 8 analog input single ended channels each providing 15 bits for a full scale deflection of 10V i.e. resolution of 0.3 millivolts and having a conversion time of 20 micro-seconds.

D/A Converter: Four 15 bit analog outputs, each having a voltage range of ±10V with an input capability of 5 milliamps TTL compatible and output up-date time of 2.4 milliseconds.

Relays: Four relay channels each having a voltage rating of 240$V_{ac}$ with current rating 1 Amp, and an operating time of 100 milliseconds.

As will be appreciated, only two of the four relay channels of relay 5 are employed in operating the reversible pump, the remainder being available at respective outputs of the unit for on/off control of auxilliary equipment.

The operation of this embodiment of the present invention will now be described in relation to dissolution rate analysis. In this case, the pump is operated such that liquid flows from each port selected to the single port.

The unit is integrated into a dissolution analysis rig having a single cell and detector, by connection of the single port to the cell inlet and introduction of the connector tubes of the selectable ports into respective sample/standard containing baths. The output of the cell detector is connected to the input to the analog to digital converter 3.

After setting up, the unit is preferably subjected to an initial test routine employing the manual control (14), to ensure that the pump and valve actuator are in working order.

Once the unit is switched for automatic operation, an analytical program sequence is supplied by the external computer C to the micro-computer 1 via the bus 2. This program may employ any or all of the selectable valve ports in any desired sequence. In accordance with this program, a current is supplied to the valve actuator 7 which in turn drives the valve 6 to the required port. A further analog voltage signal is supplied to the sensor 8 whose output passes to the computer for verification of the valve status achieved. Provided that this status is correct, the micro-computer 1 then activates the pump 9 via the relay 5, to pump liquid from the selected port to the test apparatus A. Otherwise, the micro-computer 1 instructs the valve actuator 7 to drive the valve 6 until the correct port setting is registered, before activating the pump.

The output from the detector is fed via the analog voltage input to the micro-computer 1 for processing and display. Also, the information regarding the port selected and detector response are compiled in the micro-computer 1 and displayed together at the digital display 12.

Once the analog input signal attains a steady state, the micro-computer recognizes the fact and supplies a signal to switch off the pump and then to activate the valve actuator 7 to drive the valve 6 to the next port setting.

Data obtained at the input to the micro-computer is stored until the end of the experiment and then transferred to the external computer C for dissolution rate analysis calculation. Alternatively, individual data values may be transferred to the external computer C for immediate calculation. The above described unit provides considerable benefits in dissolution rate analysis enabling samples, prepared in a commercially available dissolution bath to be automatically withdrawn and their concentration determined using a standard spectrophotometer equipped with a flow-cell.

Further, as the above described unit uses only a single test point, it has some cost advantage over multiple test point systems and will allow a variety of alternative measurement techniques to be used for dissolution rate studies.

In another such embodiment of the invention, a keypad is provided for local programing of the unit's micro-computer. This allows for pre-operation testing of the unit and, also, for direct programing of the entire operation of the micro-computer permitting such units to operate, in certain circumstances as stand alone controllers.

In the embodiment described in relation to FIG. 1 the valve actuator is pneumatic and indeed this has advantage when flammable fluids are to be handled. However, in a further preferred embodiment, the valve actuator is electrical.

Further, in the FIG. 1 embodiment, sensor 8 comprises a potentiometer. However, in a preferred embodiment the sensor 8 comprises a disc axially mounted to rotate about the axis of rotation of and with the valve, and a plurality of pairs of light emitting diodes and photo electric transistors, the diode and transistor of each pair facing one another on opposite sides of the disc. The disc has coded perforations, permitting direct determination of the actual port position of the valve to be read directly from the conduction pattern of the photo electric transistors.

Figure 2:
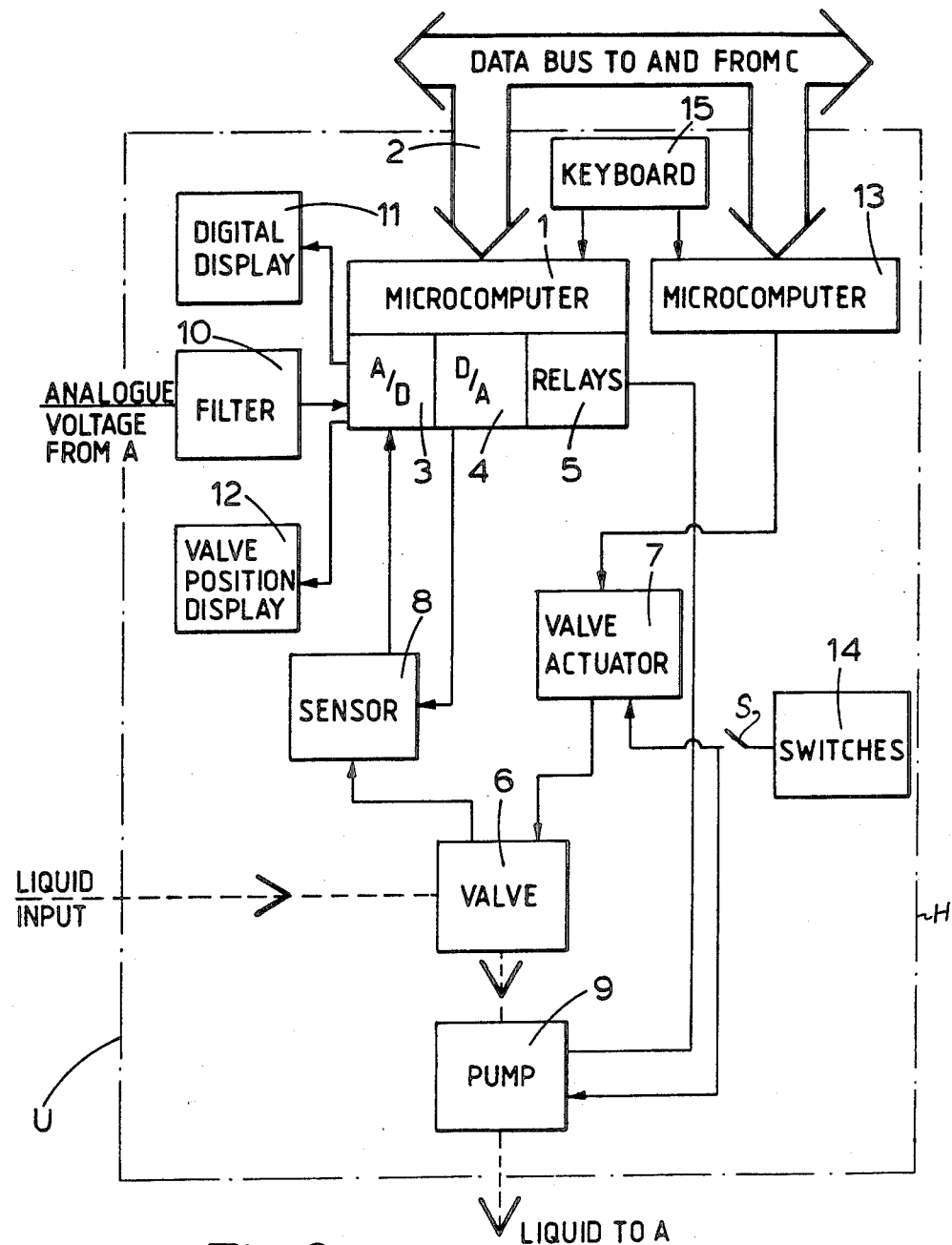
FIG. 2 shows a block diagram illustrating another embodiment of the invention.
Figure 3:
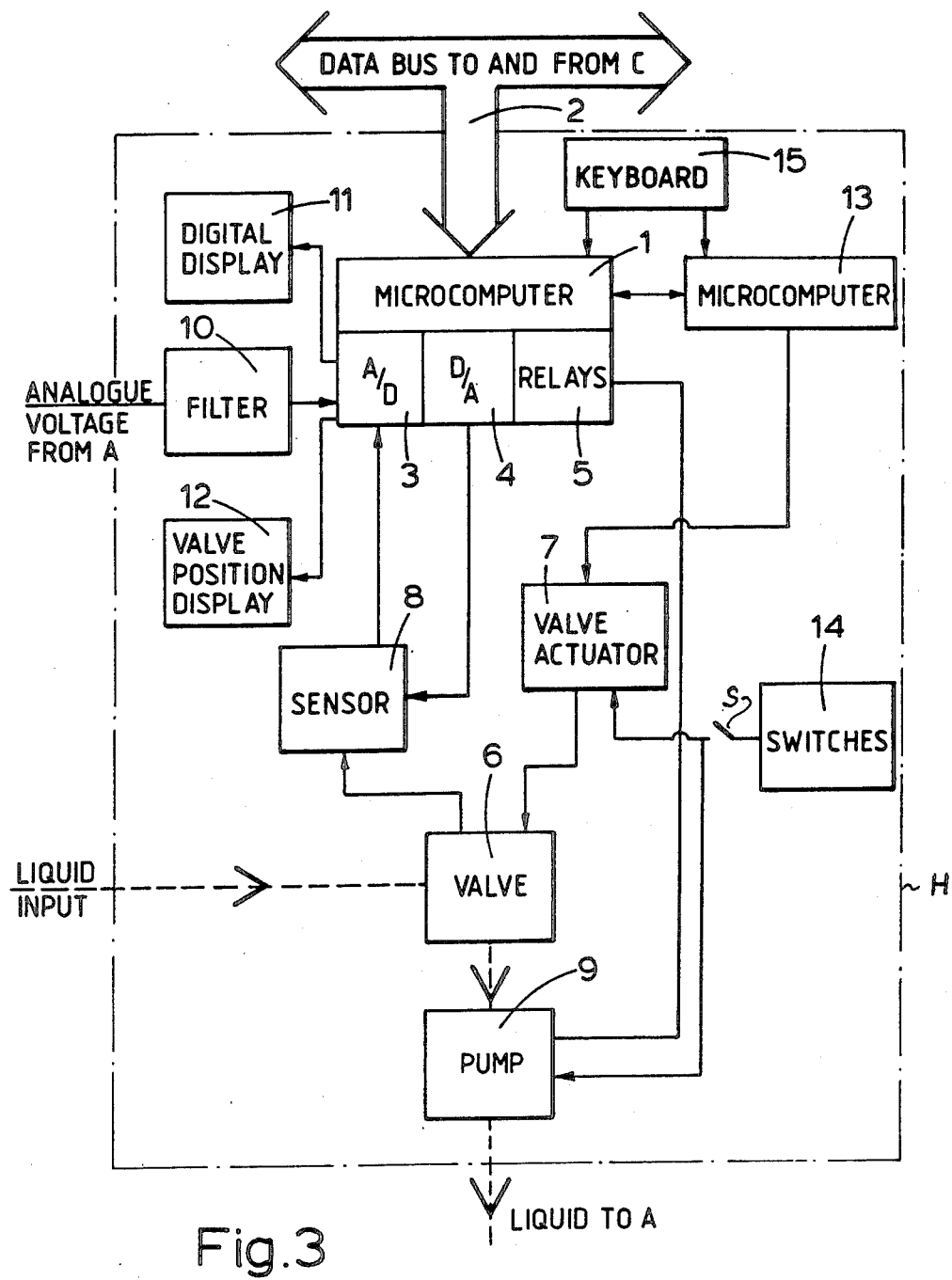
FIG. 3 shows a block diagram illustrating a preferred embodiment of the present invention.

The embodiment of the present invention illustrated in FIGS. 2 and 3 differ from that shown in FIG. 1 in that a further micro-computer 13 is provided for controlling the valve, thereby releasing capacity in the other micro-computer 1 for such tasks as monitoring and control.

In operation, these two micro-computers 1, 13 communicate with each other, micro-computer 1 relaying valve status data from sensor 8 to the micro-computer 13 and sensor activation signals and programed valve position data from the micro-computer 13 to the sensor 8 and display 12, respectively.

In the embodiment of FIG. 2, connection between the two micro-computers 1, 13 is made via the external data bus 2, while in the embodiment of FIG. 3 these micro-computers are connected via an internal bus. Thus, whereas in the embodiment of FIG. 2, the micro-computer 13 communicates directly with an external computer C for programing, in that of FIG. 3 such communication is via the micro-computer 1. As will be appreciated, the embodiment of FIG. 3 is specifically adapted for stand alone operation, in addition to operation in conjunction with an external computer.

The embodiments of FIGS. 2 and 3 also differ from that shown in FIG. 1 in that a keyboard 15 is provided for local programing of the micro-computers 1, 13 permitting pre-operation testing of the unit and also direct programing of a part of or, in the case of the embodiment of FIG. 3, the entire operation of the unit.

In the embodiments of both FIG. 2 and FIG. 3 the valve actuator is electrical rather than pneumatic. Further, the sensor 8 is of the type comprising a perforated disc and pairs of light emitting diodes and photoelectric transistors.

Figure 4:
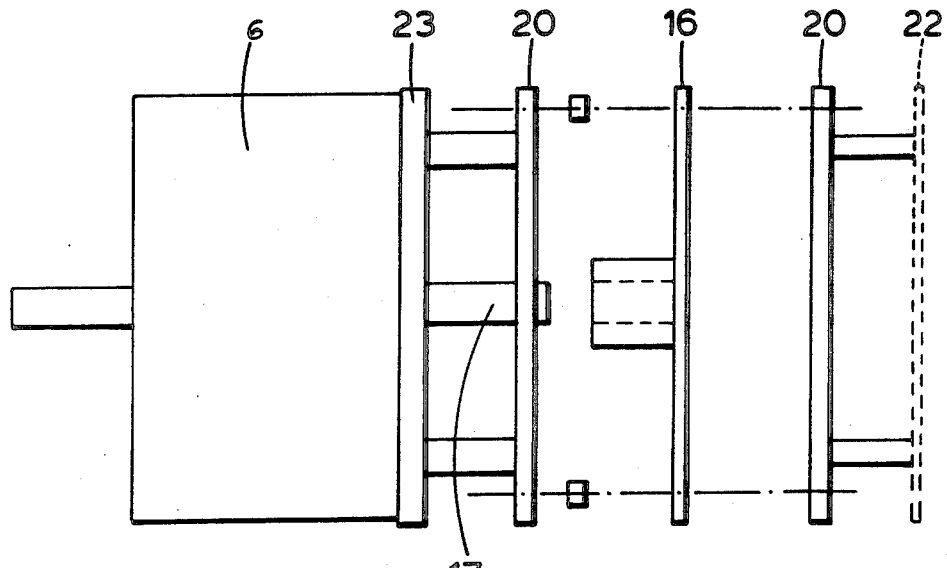
FIG. 4 illustrates, in side view, an embodiment of a valve sensor employed in the embodiments shown in FIGS. 2 and 3.
Figure 4A:
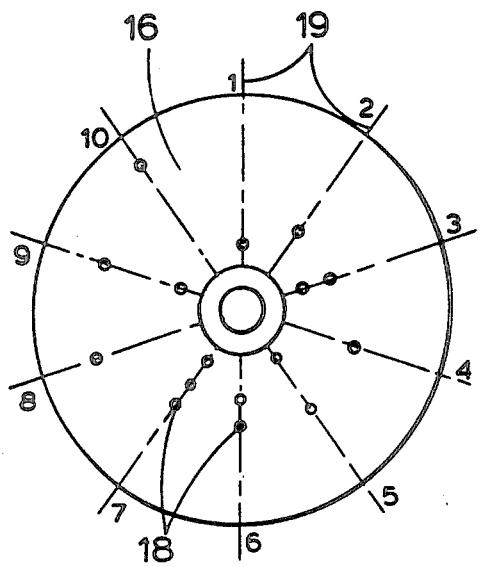
FIGS. 4A and 4B show in plan view two elements of the sensor shown in FIG. 4, and FIGS. 5A and B show schematically front and back views respectively of the external appearance of an embodiment of the present invention.
Figure 4B:
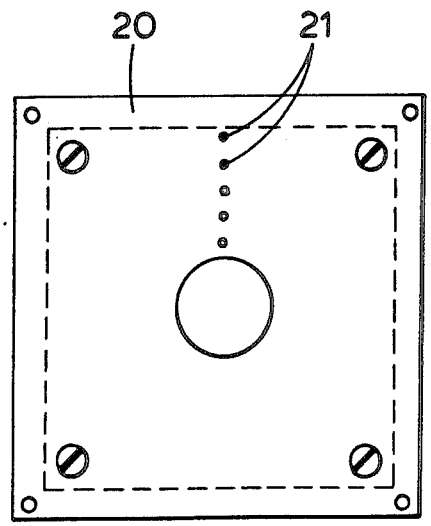

FIGS. 4, 4A and 4B illustrate the embodiment of sensor 8 employed in the units of FIGS. 2 and 3. A perforated disc 16 is mounted on a shaft 17 of the valve 6 for rotation with the valve. At least one hole 18 is provided in the disc 16 on each of ten equally spaced radii 19, where they intersect each of five concentric circles, the hole pattern on any one radius 19 being different from that on any other.

Two masking plates 20 each having an identical row of five holes 21 extending radially from their centers are rigidly mounted on either side of the disc 16 with corresponding holes in each row in alignment. The distance from the center of each plate 20 to each of the five holes 21 coresponds to the radius of a respective one of the concentric circles on which holes 18 are arranged.

Five pairs of light emitting diodes and photo electric transistors (not shown) are mounted on plates 22, 23, the diode and transistor of each pair facing one another on opposite sides of the disc 16 and in alignment with a respective pair of aligned holes 21 in the plates 20.

The disc 16 and plates 20 are mounted with respect to the valve inlet/outlet ports such that when each radius 19 of the disc 16 is aligned with the two rows of holes 21, the single port is in communication with one of the ten selectable ports. In this position the or each hole 18 on the aligned radius 19 is in alignment with corresponding holes 21 in the plates 20 permitting conduction of light between the corresponding diode-transistor pair. Since the hole pattern on any one radius 19 is unique, port alignment can be determined directly from the conduction pattern of the five transistors. Clearly, absence of conduction indicates lack of port alignment.

As will be appreciated, the overall operation of the embodiments of FIGS. 2 and 3 save as regards the points outlined above, will not differ substantially from that described in relation to FIG. 1.

Figure 5A:
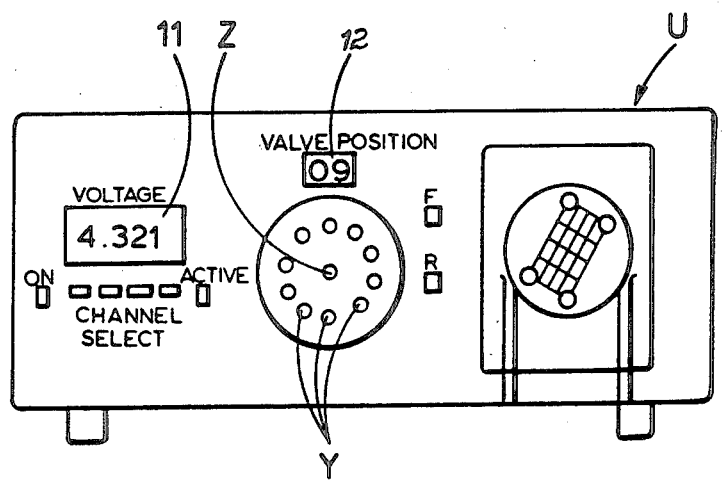
Figure 5B:
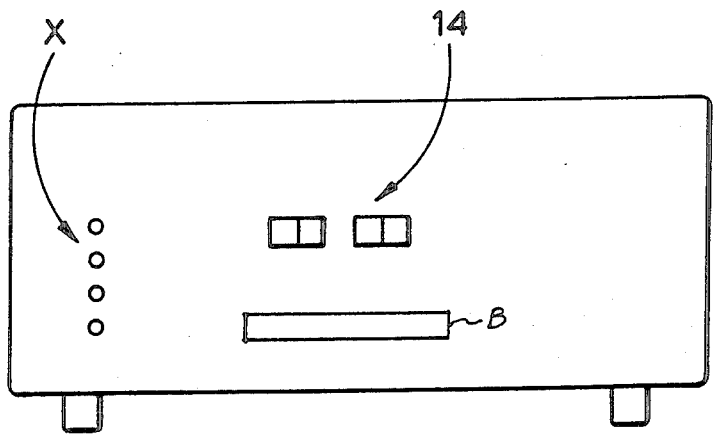

FIGS. 5A and 5B illustrate, by way of example, the external appearance of an embodiment of a unit U comprising at least one micro-computer such as described in relation to FIG. 1. References Y and Z indicate connectors for ten fluid input/output lines and a fluid output/input line respectively. FIG. 5A also indicates the view windows of displays 11 and 12. Input connectors X for up to four analog voltage input lines and switches 14 for manual operation of the pump and valve are provided on the back of the unit as can be seen in FIG. 5B.

As will be appreciated, the external computer C may control a number of the present units sequentially or simultaneously as by a cable connecting to a bus connection B on the back of the unit (FIG. 5B). The bus may be a conventional IEEE488 bus.. This arrangement facilitates programing of the units and hence has substantial cost benefits.

Further, the micro-computer 1 may be programed to operate additional devices connected to an output thereof via, for example, a respective relay 5 or via the data bus 2. Such control may be in response to the output of test/monitoring apparatus and/or the position reached in a program sequence. Thus, a plurality of such units may be used to control a complicated sequence of operations, each of which is dependent on the outcome of a preceding or subsequent operation.

In a further embodiment of the invention which also comprises a micro-computer, no external computer is employed. In this case, all operations are determined by the programing of the micro-computer.

The embodiments described above have only a single input for acquisition of data signals from the test/monitoring apparatus. In further embodiments, a plurality of such inputs are provided, permitting data acquisition from more than one detector.

The above described embodiments are adapted for interfacing analog voltage signals with an external computer. In a further embodiment, the micro-computer also has a digital input channel allowing selection of an analog or digital input in accordance with the form of the output from the test apparatus.

In the above described embodiments, the pump is a low cost peristaltic pump. For situations in which accurate dispensing of liquids is required, the unit may comprise a syringe pump.

In a further embodiment, pump control means are provided for varying the pumping rate and hence, the liquid flow rate through the valve. The operation of these control means is achieved by signals derived from the computer and supplied from an output of the digital to analog converter 4.

Although in the above embodiment, liquid is pumped from a selected one of ten ports to a single output port in certain applications, such as in the testing of a single liquid employing a plurality of reagents each in a respective test tube, the valve may be operated in the reverse mode.

The present unit may comprise more than one valve and these may be employed simultaneously or sequentially as required. By way of example, a unit comprising two valves permits the supply of a selected fluid via one valve (at predetermined intervals as determined at any time) to a selected fluid stream issuing from the other. The micro-computer and support devices of the above described embodiment are capable of controlling up to four valves.

In permitting automatic operation of test apparatus, the present unit facilitates the handling of samples not only as regards speed of processing and reduction in wastage, but also has considerable advantages as regards the handling of flammable and noxious substances by, among other things, providing a closed system.

As will be clear, the present invention permits rationalization of a wide variety of fluid systems presently used in the laboratory and elsewhere. In addition to dissolution rate analysis, the present unit may be used in many other processing applications where measurements have to be carried out on a number of discrete fluid samples or streams, at set periods. Examples of such applications include the monitoring of fermentation processes and culture growth over long periods. In the former, the progress of fermentation at various locations has to be monitored, and in the latter, the time, rate and concentration of supplying different nutrients to cultures.

This unit also has applications in sample preparation and liquid dispensing systems, ultra-violet and electrochemical testing, flow injection analysis, fraction selection and collection, liquid and gas chromatography and gas monitoring systems.

What is claimed is:

1. An adaptor unit enabling computerized operation of and data acquisition from a system, said system requiring a fluid input and being operable to supply data in electrical form at an output, said unit comprising:
   (1) a housing having at least three fluid input/output ports for connection to external fluid input/output lines, and an electrical signal input for connection to an external line providing an electrical signal input;
   (2) valve means adapted to be connected with a supply of fluid for supplying the fluid between one and a selected one of the other ports;
   (3) micro-computer means for program storage and control of the valve means;
   (4) valve actuating means connected to said valve means and said micro-computer means and being operable to position said valve means to bring said one and said selected one of said other ports into fluid communication in response to a signal from said micro-computer means;
   (5) sensor means connected to said micro-computer means and adapted to identify directly the position attained by the valve means and to communicate said position to said micro-computer means, and
   (6) means connecting the electrical signal input with the output of said system and with said micro-computer means for communicating data from said output of said system to said micro-computer means.

2. A unit as claimed in claim 1 wherein said means for communicating data to the micro-computer comprise an analog to digital converter.

3. A unit as claimed in claim 2 further comprising an analog signal filter connected between the electrical signal input and the analog to digital converter.

4. A unit as claimed in claim 1 wherein said micro-computer means comprises two micro-computers, one of which is dedicated to operating said valve actuating means.

5. A unit as claimed in claim 4 wherein said micro-computers are in communication via an integral bus.

6. A unit as claimed in claim 4 wherein each micro-computer is adapted to communicate with an external data bus.

7. A unit as claimed in claim 1 wherein said micro-computer means is adapted for communication with an external computer.

8. A unit as claimed in claim 1 further comprising an integral keyboard for programing said micro-computer means.

9. A unit as claimed in claim 1 wherein said sensor comprises a plurality of pairs of light emitting diodes and photo electric transistors and an element movable with the valve means and having coded perforations, the diodes and transistors of each pair facing one another on opposite sides of the element.

10. A unit as claimed in claim 1 wherein said micro-computer means comprise at least one relay adapted to be connected to auxiliary equipment for on-off control of the auxiliary equipment.

11. A unit as claimed in claim 1 further comprising a pump.

12. A unit as claimed in claim 8 further comprising switches for manual operation of the pump and valve actuating means.

13. A unit as claimed in claim 1 further comprising digital display means connected to an output of said micro-computer.

* * * * *